(12) United States Patent
Schwartz

(10) Patent No.: US 9,504,592 B2
(45) Date of Patent: Nov. 29, 2016

(54) ANKLE-FOOT ORTHOSIS

(71) Applicant: Nathan Schwartz, Smyrna, GA (US)

(72) Inventor: Nathan Schwartz, Smyrna, GA (US)

( * ) Notice: Subject to any disclaimer, the term of this patent is extended or adjusted under 35 U.S.C. 154(b) by 66 days.

(21) Appl. No.: 14/563,873

(22) Filed: Dec. 8, 2014

(65) Prior Publication Data

US 2015/0094637 A1 Apr. 2, 2015

Related U.S. Application Data

(62) Division of application No. 13/082,287, filed on Apr. 7, 2011, now Pat. No. 8,904,674.

(51) Int. Cl.
*A43B 7/20* (2006.01)
*A61F 5/01* (2006.01)

(52) U.S. Cl.
CPC .............. *A61F 5/0127* (2013.01); *A43B 7/20* (2013.01); *A61F 5/0111* (2013.01)

(58) Field of Classification Search
CPC ...... A43B 7/20; A61F 5/0111; A61F 5/0127
USPC .......................................... 36/89, 107, 76 R
See application file for complete search history.

(56) References Cited

U.S. PATENT DOCUMENTS

| 6,214 A | 3/1849 | Yerger |
|---|---|---|
| 589,253 A | 8/1897 | Engberg |
| 839,223 A | 12/1906 | Stevens |
| 1,236,714 A | 8/1917 | Hoppe |
| 1,332,047 A | 2/1920 | Lasher |
| 1,336,001 A | 4/1920 | Tranmer |
| 1,354,427 A | 9/1920 | Welter |
| 1,598,504 A | 6/1925 | Pierce et al. |
| 2,646,793 A | 4/1950 | Swiech et al. |
| 2,525,237 A | 10/1950 | Park |
| 2,663,294 A | 12/1953 | Harrison |
| 2,847,991 A | 8/1958 | Andrews |
| 3,064,644 A | 3/1960 | Patterson |
| 3,732,861 A | 5/1973 | Lehneis |
| 3,827,430 A * | 8/1974 | Fadden ................ A61F 5/0113 602/28 |
| 3,999,540 A | 12/1976 | Freeman |
| 4,753,229 A | 6/1988 | Sutherland |
| 4,941,273 A | 7/1990 | Gross |
| 5,052,130 A | 10/1991 | Barry et al. |
| 5,090,138 A | 2/1992 | Borden |
| 5,291,904 A | 3/1994 | Walker |
| 5,672,156 A | 9/1997 | Jimenez Ramos |
| 5,860,423 A | 1/1999 | Thompson |
| 6,102,881 A | 8/2000 | Quackenbush et al. |
| 6,319,218 B1 | 11/2001 | Birmingham |
| 6,321,469 B1 | 11/2001 | Cretinon |
| 6,423,021 B1 | 7/2002 | Gallegos |
| 6,824,523 B2 | 11/2004 | Carlson |
| 6,887,213 B2 | 5/2005 | Smits |

(Continued)

*Primary Examiner* — Marie Bays
(74) *Attorney, Agent, or Firm* — Scott A. Hill; The Hill Law Firm, PLC

(57) ABSTRACT

An Ankle-Foot Orthosis, or AFO, has a vertical portion and a horizontal portion joined together. The horizontal portion is fixed to a shoe, which is selected by a user, by separating at least part of the sole such that the horizontal portion can be adhered near or between a midsole of the sole of a shoe. The horizontal portion provides the necessary structure needed to connect a shoe to the vertical portion of the AFO such that a user suffering with a weakness or deformity can walk with a more normal gait. In an alternate embodiment, the AFO is removable from a shoe such that it can be replaced onto the same or a different shoe.

12 Claims, 5 Drawing Sheets

(56) References Cited

U.S. PATENT DOCUMENTS

| | | |
|---|---|---|
| 7,112,180 B2 * | 9/2006 | Guenther .............. A61F 5/0113 128/882 |
| 7,112,182 B1 | 9/2006 | Zahiri |
| 7,219,450 B2 | 5/2007 | Langley |
| 7,267,657 B1 | 9/2007 | Mitchell |
| 7,270,644 B2 | 9/2007 | Ingimundarson |
| 7,364,561 B1 | 4/2008 | Morton |
| 7,513,880 B2 | 4/2009 | Ingimundarson et al. |
| 8,904,674 B2 * | 12/2014 | Schwartz ................. A43B 7/20 36/107 |
| 2010/0101118 A1 * | 4/2010 | Guenther .............. A61F 5/0111 36/140 |

* cited by examiner

ANKLE-FOOT ORTHOSIS

This application is a divisional application of and claims priority to pending U.S. patent application Ser. No. 13/082,287, filed Apr. 7, 2011, entitled "Ankle-Foot Orthosis".

BACKGROUND OF THE INVENTION

Ankle-Foot Orthoses (AFOs) are braces that structurally compensate for weak or deformed ankle joints. Typically, an AFO will limit the range of motion of an ankle to prevent the foot from dropping or rotating into a position that hinders walking. Ankle braces dating back fifty years or more were commonly constructed from metal frames with leather straps. Shoes typically were characterized by prominent heels, with a heel breast that could engage a stirrup, so early ankle braces often attached to or around a heel structure.

Over the decades, shoe structures and materials have evolved considerably. Typical modern footwear has become relatively more flexible and compliant compared to footwear contemporary to earlier foot braces. With few exceptions, modern shoes no longer have a heel structure to use as a point of attachment. In addition, a focus on comfort in the construct of the sole of modern footwear has led to the use and development of resilient synthetic materials, sometimes containing foams or gels, for added cushioning. This development, although preferable for shoe comfort, poses specific challenges to cutting-edge shoe orthosis companies.

SUMMARY OF THE INVENTION

The present invention is an Ankle Foot Orthosis, or AFO, that is fixed to a shoe. Throughout this description, the term shoe includes any footwear characterized by a sole and an upper, the shoe generally being used for walking Because there are so many different shoe styles to choose from, it is desirable to be able to modify a wearer's existing choices of shoes such that a wearer can experience exceptional stability without diminishing the fit of the shoe. Many wearers of AFOs suffer from a loss of sensation, so previous modern AFOs that incorporate hard plastic into the interior of a shoe can result in ulceration and other problems that a wearer can avoid by using the present invention. After separating at least a portion of the outsole from the rest of the sole, a horizontal portion of the preferred AFO is inserted into the sole before reattaching the outsole. When a vertical portion of an AFO is strapped to the leg of a wearer, the AFO provides assistance to those suffering from a weak or unstable ankle condition, such as foot drop or other neurogenic or congenital palsies.

Figure 1:
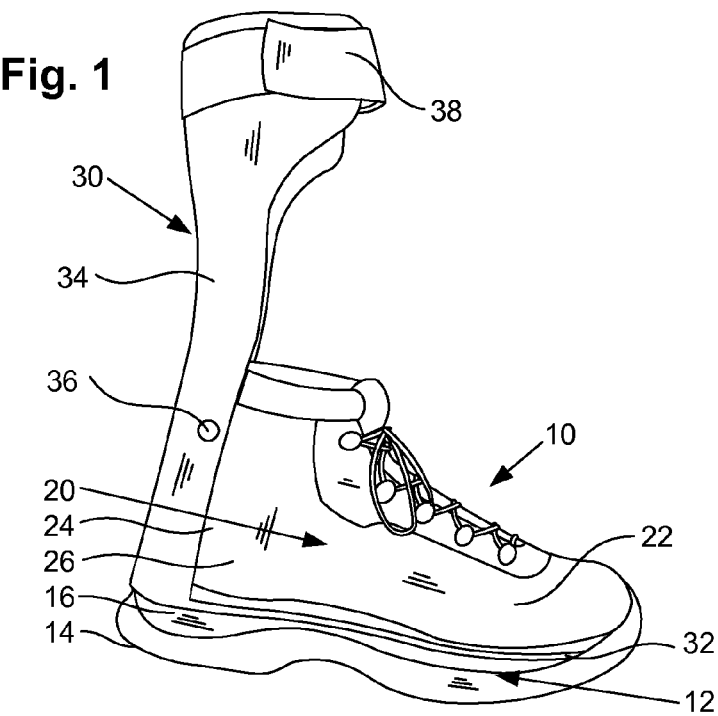
FIG. 1 is perspective view of a shoe incorporating a preferred embodiment of the present invention.
Figure 2:
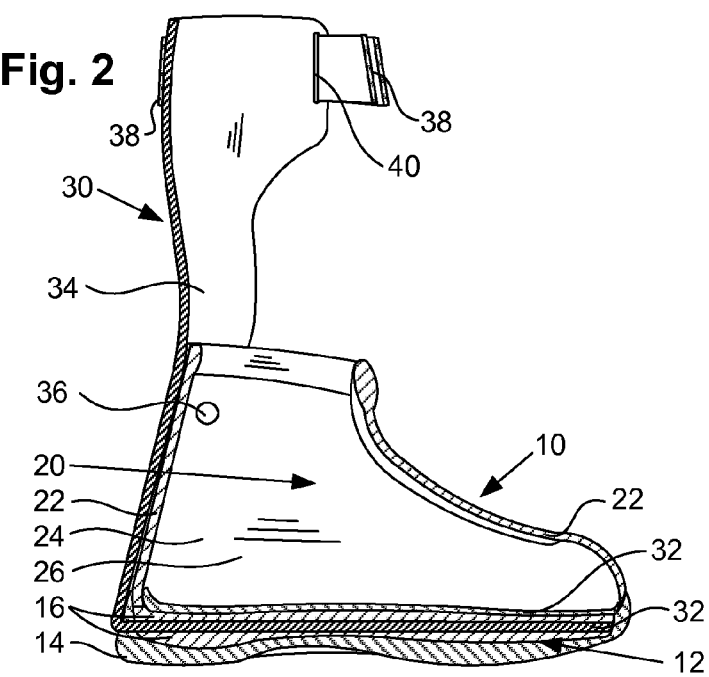
FIG. 2 is vertical sagittal section through the shoe and AFO of FIG. 1.
Figure 3:
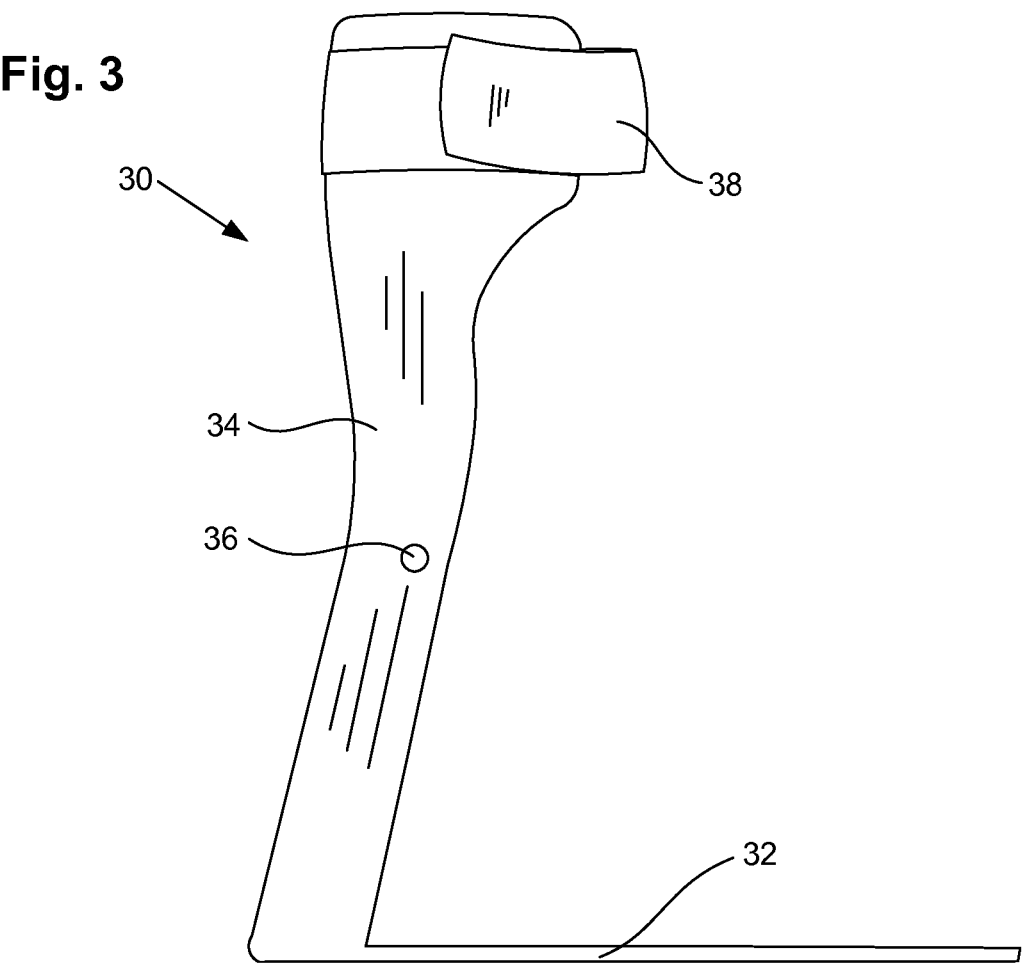
FIG. 3 is a side view of the AFO used in FIG. 1.
Figure 4:
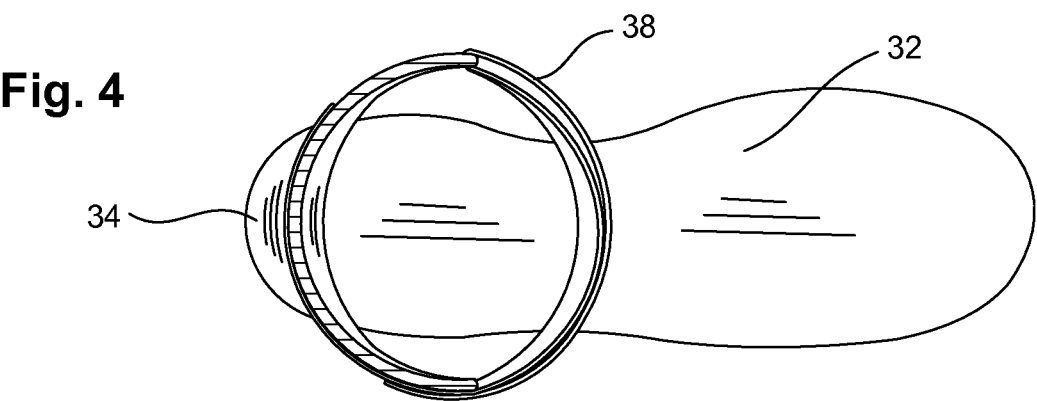
FIG. 4 is a top view of the AFO used in FIG. 1.

The following is the list of numerical callouts used in FIGS. 1-11:

10 Shoe
12 Sole
14 Outsole
16 Midsole
18 Insole
20 Upper
22 Vamp
24 Quarter
26 Rear
28 Sides
30 Ankle-Foot Orthosis
32 Horizontal portion
34 Vertical portion
36 Fastener
38 Strap
40 Slot
44 Channel portion
46 Upwardly bent section
48 Hinge
50 Pad
52 Joint stop
54 Button
56 Pins
58 Flared portion
60 Stud
62 Rivet
64 Groove
66 Aperture
68 Ankle strap

DETAILED DESCRIPTION OF THE INVENTION

This detailed description will describe the present ankle-foot orthosis (AFO) substantially from the bottom up, as assembled. Throughout the remainder of this description, the term "bottom" refers to that surface or portion of a part or feature that is relatively closest to the bottom of a referenced figure. Generally, an AFO 30 has a horizontal portion 32 that is fixed to a shoe 10, and a vertical portion 34 that is strapped to a wearer's calf or shin. In the most preferred embodiment, a midsole of a shoe is cut apart along a horizontal plane such that the horizontal portion of the AFO can be adhered into the midsole 16, and the vertical portion of the AFO is fastened to the quarter 24 of the shoe. A common hook-and-loop strap 36 is used to secure the vertical portion to the leg of a wearer. Alternate embodiments, shown in FIGS. 5-11, will also be described. Where reference numbers in one figure are the same as another figure, those reference numbers carry substantially the same meaning Preferred sizes, materials and methods of attachment will be discussed, but these preferences are not intended to exclude other suitable or functionally equivalent sizes, materials or methods of attachment.

A shoe 10 that incorporates the present invention is characterized by a sole 12 and an upper 20. Examples of shoes include athletic shoes, men's shoes, women's shoes, boots and other footwear commonly used for walking. The sole, which is the part of a shoe below a wearer's foot, is comprised of an outsole 14 that is fixed to the bottom of a midsole 16 that is covered by an insole 18. The outsole is the part of the sole that contacts the ground, the midsole is one or more layers that adds cushion and support to the sole, and the insole is the comfortable part of the sole that contacts the bottom of a wearer's foot. The upper, which is the part of a shoe that covers a wearer's foot, includes a vamp 22 for covering the front of the foot and a quarter 24 for covering the heel of the foot. The quarter has a rear 26 and sides 28 that wrap around the heel of a wearer.

The preferred ankle-foot orthosis (AFO) 30 has a horizontal portion 32 and a vertical portion 34 joined together. In the most preferred embodiment, shown in FIGS. 1-4, the entire AFO structure is made from a plastic such that the horizontal portion and vertical portion are a continuous, one-piece molded or thermo-formed construction. Other suitable materials include but are not limited to, high performance resins, thermoplastics or other synthetic materials, especially those that can be combined with tougheners to provide higher impact resistance, with pigments and UV stabilizers to provide and maintain a desired appearance, with glass fibers to provide higher stiffness, or with Teflon® or Kevlar® to provide improved wear and friction characteristics. Combinations of materials can also be used, such as a plastic vertical portion with a spring steel horizontal portion, or any other desired combination of materials to form the horizontal and vertical portions as dictated by the needs of users in a customizable fashion. When a common plastic is used, such as polypropylene, polyethylene or polyvinylchloride, it can be approximately one to four millimeters in thickness. The thickness and materials can be varied proportionately to the demands of strength, durability and flexibility for the needs of the user. For example, the proximal end of the vertical portion can be thinner and more flexible so as not to impede the mechanics of the user's gait, whereas, by way of additional example, the vertical portion surrounding a user's heel may be of a thicker and more heavy-duty construction appropriate to a stress and weight-bearing functionality.

The horizontal portion 32 of the AFO 30 is essential for shoes that are lacking the rigidity historically provided by a shank, which is typically minimal or absent in modern footwear, such as a running shoe. Removal of a volume of the midsole 16 equivalent to the inserted volume of the horizontal portion of the AFO avoids addition of undesired asymmetric height relative to the contra lateral shoe. Another concern would involve those shoes having a midsole design that has a specific function, such as a honeycomb design for cushioning. In this instance, it would be sub-optimal to cut through the midsection of such a midsole, as the function will likely be compromised in the process. Attaching the horizontal portion of the AFO above or below such a midsection structure would circumvent this concern. In any case, the horizontal portion of the AFO would be inserted at an optimal location after separating the sole to create a separation between the outsole 14 and insole 18 of a user's shoe 10.

The horizontal portion 32 of the AFO 30 preferably is adjoined to the vertical portion 34 of the AFO in a contiguous fashion slightly exterior to the posterior aspect of the shoe 10. Alternatively, depending on anatomic considerations, adjoinment can be at a lateral or medial aspect of the shoe. If the horizontal portion and vertical portion of the AFO adjoin posterior to the shoe, they will need to do so at an acute angle so as not to impede the natural mechanics of gait. If the point at which the horizontal portion and vertical portion of the AFO adjoin is at a medial or lateral aspect of the shoe, then the angle of adjoinment can be at or approximately ninety degrees.

The vertical portion 34 of the AFO 30 is secured to the quarter 24 of a user's shoe 10, preferably at the rear 26 of the quarter, but additionally or alternatively secured to one or both sides 28 of the quarter. The vertical portion can be fastened to the quarter with any suitable fastener 36, such as a rivet, but alternatively could be affixed with an adhesive substance, or even attached via stitching. The form of the vertical portion of the AFO is anatomically structured to mimic the contour of a user's lower leg, optimally along the posterior calf. Alternatively, the vertical portion could extend proximally along the lateral or medial calf, or along the shin. However, in the absence of specific deformities, the posterior calf would likely provide the greatest tissue compressibility and padding. The material thickness comprising the vertical portion of the AFO can be varied as desired. For example, the material could be tapered superiorly to allow more flexibility where strength and durability are relatively less crucial compared to the inferior end of the vertical portion of the AFO, where thicker materials will allow the point of attachment area to withstand intensified forces, such as shear, compression and torque forces characteristic of the mechanisms of walking with an AFO. Allowing the vertical portion to flex slightly, by selecting an appropriate material and thickness relative to the weight of a user, contributes to dorsiflexion.

The vertical portion 34 can be secured around the user's lower leg by many different alternate methods, depending on the anatomy of the user's lower leg and the desired proximity of the securing method. Methods can include straps secured by buckle mechanisms, hook and loop fasteners or snap fasteners, laces, or other means. A preferred strap 38, most clearly shown in FIGS. 1-4, has a hook and loop fastener fabric affixed to the outer surface of the vertical portion of the AFO, and a free end of the strap is passed through a slot 40 in the vertical portion such that the strap can overlap and fasten to itself to maximize adjustability. Foam or other comfortable materials, not shown, can be fixed to the inner surface of the vertical portion of the AFO as desired for improved comfort.

Figure 5:
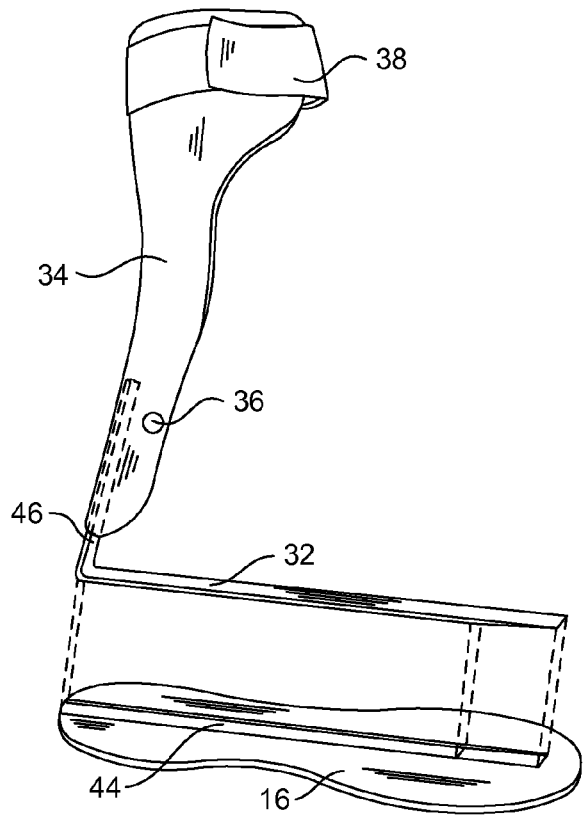
FIG. 5 is a perspective view of an alternate embodiment of a midsole and AFO of the present invention.

In the alternate embodiment shown in FIG. 5, the horizontal portion 32 is substantially a shank that can be installed into a fitted channel portion 44 cut into the midsole 16 of a shoe 10. Because midsoles can be any number of layers, where a particular midsole is separated to install an AFO will vary. The portion of the midsole shown in FIG. 5 does not necessarily represent the entire midsole of a shoe, so additional midsole material may overlay the horizontal portion shown after the shoe is reassembled. When a strong material is used, such as spring steel, the horizontal portion can be thin such that it can be install against midsole materials that are soft enough to deform, rather than needing to cut, a channel portion into the midsole. Installing the horizontal portion near or against the bottom of a midsole should result in the best comfort to a user if the channel portion is deformed rather than cut into the midsole. Adjoinment of the horizontal portion and the vertical portion 34 of this alternate embodiment of the AFO 30 can as already described, or, where the material of the horizontal portion and vertical portion are different, insert molding or overlapping of materials can be used to join portions of the AFO.

FIG. 5 shows a spring steel horizontal portion that has an upwardly bent section 46 that follows the rear 26 of the quarter 24 of a shoe 10, and a plastic vertical portion overlaps the upwardly bent section of spring steel such that the vertical and horizontal portions can be fastened together, such as with rivets.

Figure 6:
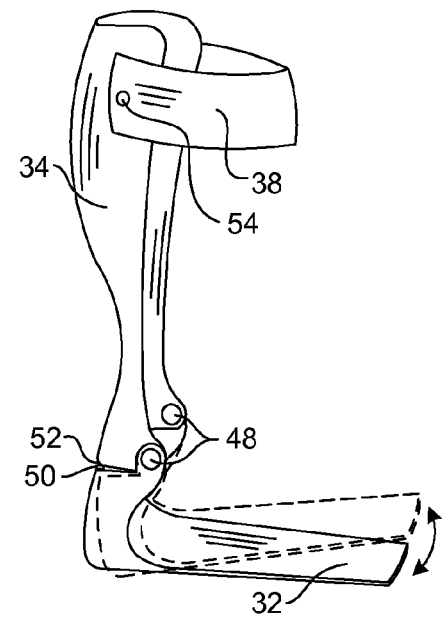
FIG. 6 is a perspective view of an alternate embodiment of the present invention, characterized by a hinged ankle joint.

In the alternate embodiment shown in FIG. 6, the vertical portion 34 of the AFO 30 is characterized by a hinge 48 superior to where the vertical portion adjoins the horizontal portion 32, the hinge substantially approximating an ankle joint, allowing for flexion-extension of the AFO inferior to the hinge. The hinge can be spring-loaded with a resilient material to return the AFO to a dorsiflexed position after each step/extension imparted by the user. Additionally, an elastic pad 50 can be inserted along one or both opposing edges of a joint stop 52. The joint stop is composed of inferior and superior segments that prevent the horizontal portion of the AFO from excessively dropping, which in turn prevents a foot from excessively dropping during gait. The pad between the opposing edges of the joint stop will dampen impact forces and prevent audible contact of the joint stop materials during ambulatory range of motion. By way of additional example, an alternate elastic strap 38 that fastens around a user's leg using a simple button 54 is shown at the top of the vertical portion of the AFO.

Figure 7:
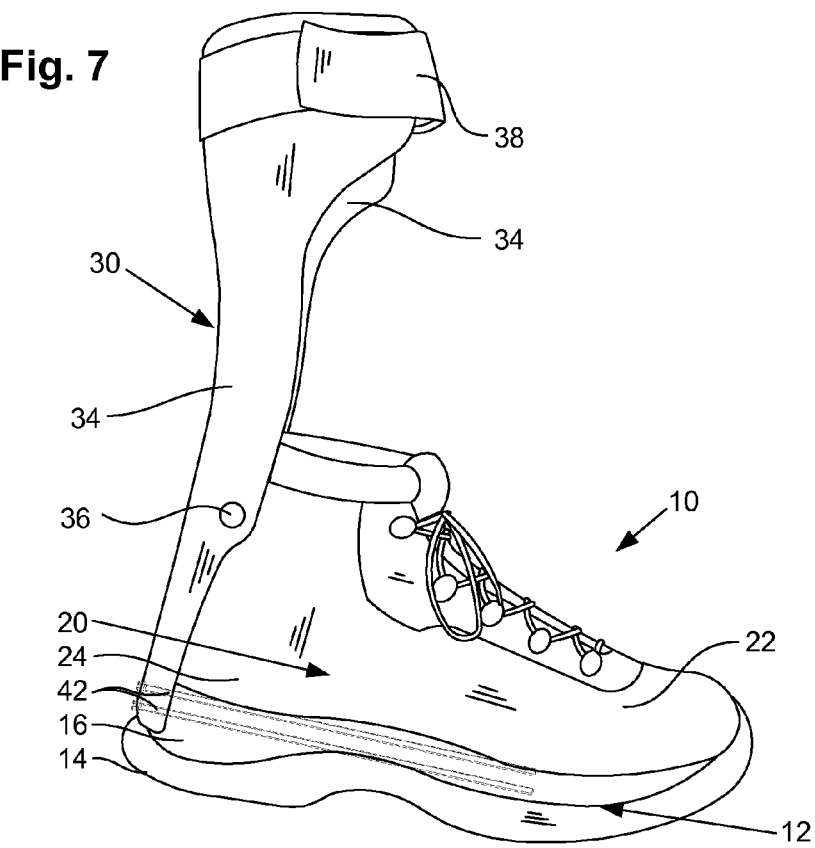
FIG. 7 is a perspective view of an alternate embodiment characterized by at least two long pins secured into the midsole of a shoe.
Figure 8:
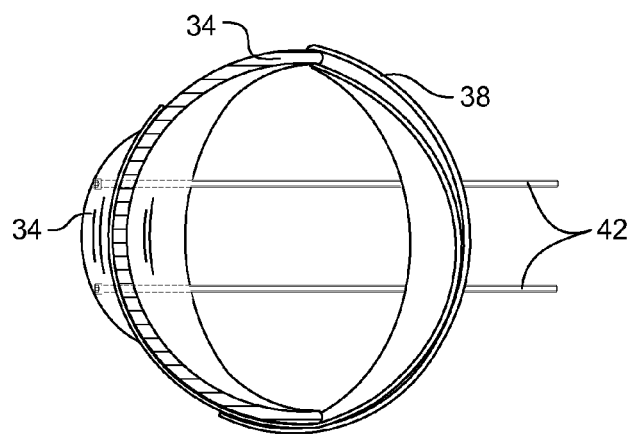
FIG. 8 is a top view of the AFO device used in FIG. 7.

In the alternate embodiment shown in FIGS. 7 and 8, the horizontal portion 32 is characterized by long pins 56 that are anchored into the midsole 16 of a shoe 10. Holes can be pre-drilled or otherwise formed into the midsole such that the pins can easily be inserted. The long pins can be self tapping screws, but some midsole materials may not accept such an installation. An adhesive can be used to additionally secure the pins into the midsole. The pins can have flared heads, threads, or other fastener means for securing the horizontal portion of the AFO to the vertical portion 34. The vertical portion can additionally be secured to the quarter 24 of a shoe using one or more fasteners 36 or adhesive.

Figure 9:
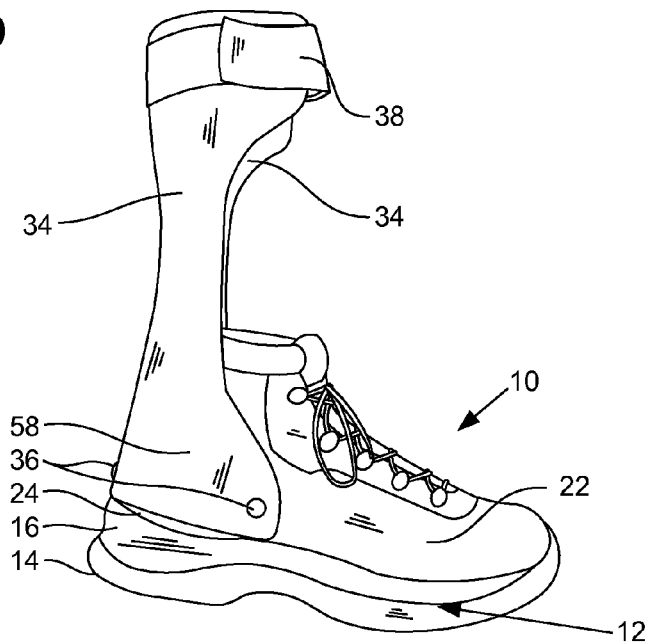
FIG. 9 is a perspective view of an alternate embodiment of the present invention that is secured to the quarter of a shoe.

In the alternate embodiment shown in FIG. 9, the inferior section of the vertical portion 34 of the AFO 30 is augmented by a flared portion 58 which forms a wrap around the quarter 24 of a shoe 10. Structurally, the flared portion is a substitute for a horizontal portion for a shoe that has a relatively stiff sole and upper. In this scenario, fasteners 36 are fastened to points that are medial, posterior and lateral points of attachment on the shoe's quarter 24. Consequently, the immobilization of the user's ankle and the anteriorly-adjusted points of circumferential attachment serve to create a functional equivalent of the vertical portion and horizontal portion combination of the preferred embodiment. This alternate embodiment, although possibly less aesthetic and hidden than the preferred embodiment, may have the advantage of being easier to install. Installation could be permanent and non-reversible, or may be by a method that would allow attachment and detachment at will by the user, such as via screw caps onto threaded pegs, metal clasps, etc.

Figure 10:
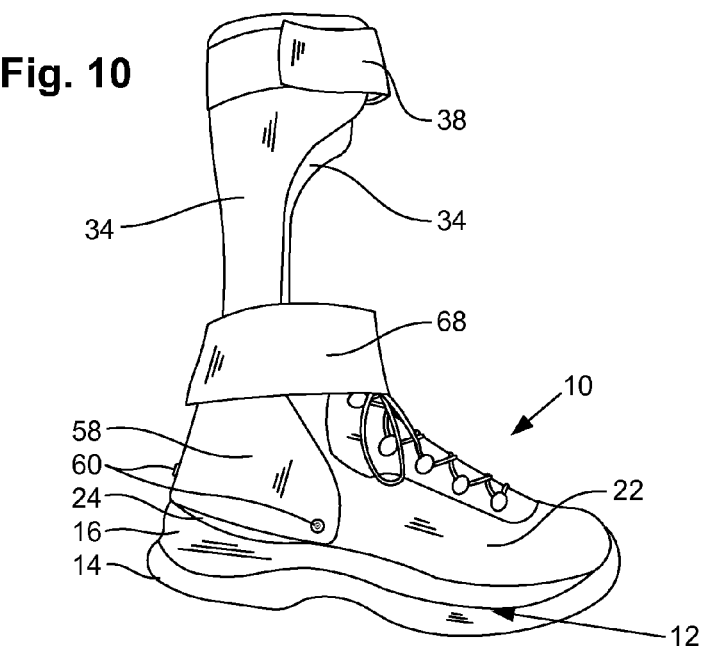
FIG. 10 is a perspective view of an alternate embodiment of an AFO, similar to the one in FIG. 9, except that press studs are used to removably fasten the AFO to the shoe such that the AFO can be reattached to the same or another shoe.
Figure 11:
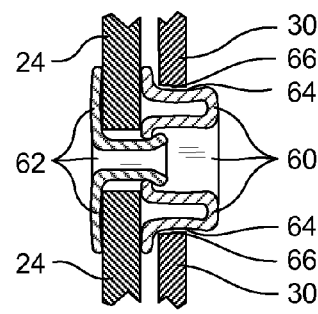
FIG. 11 is a vertical cross-section through a press stud used to secure the AFO in FIG. 10 to a shoe.

In the alternate embodiment shown in FIGS. 10 and 11, an AFO 30 similar to the one shown in FIG. 9 is removably attached to a shoe that preferably has three studs 60 fastened to the quarter 24 of a first shoe 10 using rivets 62, or another suitable fastener means. Each stud, which projects outwardly, is preferably characterized by a groove 64 that snaps into an aperture 66 formed in the flared portion 58 of the AFO. To install an AFO onto a first shoe equipped with studs, the flared portion of the AFO is pulled around the quarter of a shoe until a stud in the rear 26 of the quarter of the shoe snaps into the aperture at the posterior of the AFO. Next, apertures in the lateral and medial sides of the AFO are aligned over studs in the sides 28 of the quarter of a shoe, and the studs are snapped into the apertures. An ankle strap 68 is provided for securing the AFO around the ankle of a user. The bottom of the AFO is also preferably narrower than a shoe such that the AFO clamps around the quarter of a shoe, further securing the studs into the apertures. It should be noted that the stud at the rear of the quarter is unlikely to separate while the studs at the sides of the quarter are secured to the AFO. The AFO can easily be removed by unsnapping the studs. To equip a second shoe with studs, simply allowing the AFO to clamp around the quarter of the second shoe should allow someone to easily mark the required location of studs by passing a marker through the apertures in the AFO, and then riveting the studs into the quarter of the second shoe at the marker points.

While a preferred form of the invention has been shown and described, it will be realized that alterations and modifications may be made thereto without departing from the scope of the following claims.

What is claimed is:

1. A method for fixing an ankle foot orthosis (AFO) to a shoe comprising the steps of:
    selecting a pair of shoes for a wearer;
    separating at least a portion of a sole of a shoe of the pair to create a separation;
    aligning a vertical portion of the AFO at least partially adjacent a portion of an upper of the shoe;
    aligning a horizontal portion of the AFO substantially adjacent the separation;
    fixing the horizontal portion substantial in or adjacent the separation; and
    wherein the step of separating is characterized by cutting at least half of a midsole along a substantially horizontal plane.

2. The method of claim 1 further comprising the step of removing a thickness of at least a portion of the midsole.

3. A method for fixing an ankle foot orthosis (AFO) to a shoe comprising the steps of:
    selecting a pair of shoes for a wearer;
    separating at least a portion of a sole of a shoe of the pair to create a separation;
    aligning a vertical portion of the AFO at least partially adjacent a portion of an upper of the shoe;
    aligning a horizontal portion of the AFO substantially adjacent the separation;
    fixing the horizontal portion substantial in or adjacent the separation; and
    cutting a channel into a portion of a midsole, the channel being substantially the same size and thickness as the horizontal portion of the AFO.

4. A method for fixing an ankle foot orthosis (AFO) to a shoe comprising the steps of:
    selecting a pair of shoes for a wearer;
    separating at least a portion of a sole of a shoe of the pair to create a separation;
    aligning a vertical portion of the AFO at least partially adjacent a portion of an upper of the shoe;
    aligning a horizontal portion of the AFO substantially adjacent the separation;
    fixing the horizontal portion substantial in or adjacent the separation; and
    wherein the step of separating is characterized by making a substantial planar horizontal cut the entire length of a midsole of the shoe.

5. The method of claim 3 wherein the step of fixing is characterized by removably attaching the vertical portion to the horizontal portion; and further comprising the step of fixing the vertical portion to a second horizontal portion of a second shoe.

6. A method for fixing an ankle foot orthosis (AFO) to a shoe comprising the steps of:
   selecting a pair of shoes for a wearer;
   separating at least a portion of a sole of a shoe of the pair to create a separation;
   aligning a vertical portion of the AFO at least partially adjacent a portion of an upper of the shoe;
   aligning a horizontal portion of the AFO substantially adjacent the separation;
   fixing the horizontal portion substantial in or adjacent the separation; and
   fastening the vertical portion of the AFO to the upper using at least one fastener.

7. A method for adding an ankle foot orthosis (AFO) to a shoe comprising the steps of:
   selecting a pair of shoes for a wearer;
   selecting an AFO characterized by a vertical portion and a horizontal portion;
   cutting at least a portion of a sole of a shoe of the pair to create a separation;
   positioning the horizontal portion in the separation such that a portion of the vertical portion is substantially adjacent a rear of a quarter of an upper of the shoe;
   adhering the separation together such that the horizontal portion is fixed in the separation; and
   wherein the step of cutting is characterized by cutting at least half of a midsole of the sole along a substantially horizontal plane.

8. A method for adding an ankle foot orthosis (AFO) to a shoe comprising the steps of:
   selecting a pair of shoes for a wearer;
   selecting an AFO characterized by a vertical portion and a horizontal portion;
   cutting at least a portion of a sole of a shoe of the pair to create a separation;
   positioning the horizontal portion in the separation such that a portion of the vertical portion is substantially adjacent a rear of a quarter of an upper of the shoe;
   adhering the separation together such that the horizontal portion is fixed in the separation; and
   removing a thickness of at least a portion of the midsole.

9. A method for adding an ankle foot orthosis (AFO) to a shoe comprising the steps of:
   selecting a pair of shoes for a wearer;
   selecting an AFO characterized by a vertical portion and a horizontal portion;
   cutting at least a portion of a sole of a shoe of the pair to create a separation;
   positioning the horizontal portion in the separation such that a portion of the vertical portion is substantially adjacent a rear of a quarter of an upper of the shoe;
   adhering the separation together such that the horizontal portion is fixed in the separation; and
   cutting a channel into a portion of a midsole of the sole, the channel being substantially the same size and thickness as the horizontal portion of the AFO.

10. A method for adding an ankle foot orthosis (AFO) to a shoe comprising the steps of:
    selecting a pair of shoes for a wearer;
    selecting an AFO characterized by a vertical portion and a horizontal portion;
    cutting at least a portion of a sole of a shoe of the pair to create a separation;
    positioning the horizontal portion in the separation such that a portion of the vertical portion is substantially adjacent a rear of a quarter of an upper of the shoe;
    adhering the separation together such that the horizontal portion is fixed in the separation; and
    forming an upwardly bent portion in the horizontal portion; and removably fixing the upwardly bent portion to the vertical portion of the AFO.

11. The method of claim 10 further comprising the step of removing the vertical portion from the shoe; and removably fixing the vertical portion to a different shoe.

12. A method for adding an ankle foot orthosis (AFO) to a shoe comprising the steps of:
    selecting a pair of shoes for a wearer;
    selecting an AFO characterized by a vertical portion and a horizontal portion;
    cutting at least a portion of a sole of a shoe of the pair to create a separation;
    positioning the horizontal portion in the separation such that a portion of the vertical portion is substantially adjacent a rear of a quarter of an upper of the shoe;
    adhering the separation together such that the horizontal portion is fixed in the separation; and
    fastening the vertical portion of the AFO to the upper using at least one fastener.

* * * * *